United States Patent
Unsworth et al.

(10) Patent No.: US 6,620,126 B2
(45) Date of Patent: *Sep. 16, 2003

(54) VARIABLE SHAPE GUIDE APPARATUS

(76) Inventors: John D. Unsworth, 7 Innovation Dr., Suite 107, Flamborough, Ontario (CA), L9H 7H9; Thomas C. Waram, 7 Innovation Dr., Suite 107, Flamborough, Ontario (CA), L9H 7H9

( * ) Notice: Subject to any disclaimer, the term of this patent is extended or adjusted under 35 U.S.C. 154(b) by 0 days.

This patent is subject to a terminal disclaimer.

(21) Appl. No.: 09/867,762

(22) Filed: May 31, 2001

(65) Prior Publication Data

US 2002/0013550 A1 Jan. 31, 2002

Related U.S. Application Data

(63) Continuation-in-part of application No. 09/477,640, filed on Jan. 5, 2000.

(51) Int. Cl.[7] .................. A61M 31/00; A61M 37/00
(52) U.S. Cl. ............... 604/95.05; 604/113; 604/530; 604/531
(58) Field of Search .................. 604/113, 264, 604/523, 524, 525, 528, 95.05, 530–532; 606/108, 78

(56) References Cited

U.S. PATENT DOCUMENTS

| | | | |
|---|---|---|---|
| 4,930,494 A | * | 6/1990 | Takehana et al. ........... 600/145 |
| 5,334,168 A | | 8/1994 | Hemmer |
| 5,531,685 A | | 7/1996 | Hemmer |
| 5,846,247 A | * | 12/1998 | Unsworth et al. .......... 606/108 |
| 6,533,752 B1 | * | 3/2003 | Waram et al. ........... 604/95.05 |

FOREIGN PATENT DOCUMENTS

EP    0 279 316 A    8/1988

* cited by examiner

Primary Examiner—Michael J. Hayes
Assistant Examiner—Catherine Serke

(57) ABSTRACT

An apparatus having a steerable distal end portion for insertion in a body lumen comprises a superlastic shape memory member which adopts a memorized shape in an unloaded austenitic state, and stationary heating means for heating at least a portion of the superlastic shape memory member to a temperature above the temperature inside the body lumen. Heating the superlastic shape memory member inside the body lumen causes it to increase in stiffness and tend toward the memorized shape, and subsequent discontinuation of heating causes the superlastic shape memory member to decrease in stiffness, allowing the distal end portion to be deformed from the memorized shape, thereby resulting in movement of the distal end portion which assists in steering it through the body lumen. Preferably, the elongate shape memory member is tubular, having a lumen extending therethrough, and the heating means comprises electrical heating means. In a particularly preferred embodiment, the heating means comprises electrical supply means and electrical conductor means extending through the lumen of the superlastic shape memory member.

27 Claims, 3 Drawing Sheets

VARIABLE SHAPE GUIDE APPARATUS

REFERENCE TO RELATED APPLICATIONS

This application is a continuation-in-part application of U.S. patent application Ser. No. 09/477,640, filed on Jan. 5, 2000, pending.

FIELD OF THE INVENTION

This invention relates to steerable catheters, cannulae, guides and the like, that are designed to be steered through body cavities and aimable at obstructions, organs, or tissues within the body from a position external from the body.

BACKGROUND OF THE INVENTION

A great deal of research has been directed at developing a catheter or guide having a distal end which, when inserted into a body, is readily steerable and aimable to advance the device through body cavities and passageways. It has been observed that materials exhibiting mechanical memory properties triggered by heat are particularly useful for enhancing the maneuverability of catheters of like devices. These materials are commonly called "temperature-activated memory materials" or "shape memory alloys" (SMA), because they move to assume a predetermined shape when heated to a predetermined temperature.

Shape memory among metallic alloys is a result of the fact that the alloy undergoes a reversible solid state phase transformation between an austenitic state and a martensitic state with a change in temperature. This transformation is sometimes referred to as a thermoelastic martensitic transformation. An article made from such a SMA, for example a wire, is easily deformed from its original high temperature or austenitic configuration to a new configuration when cooled below the temperature at which the alloy is transformed from the austenitic state to the martensitic state. The temperature at which this transformation begins is usually referred to as the martensite start ($M_s$) temperature, and upon continued cooling the temperature at which it finishes, the martensite finish ($M_f$) temperature. The wire changes from a rigid state with a relatively high yield strength, in its austenitic form, to a state in which it is easily deformable, with a relatively low yield strength, in its martensitic form, in which it is able to sustain significant plastic-like deformation, at an almost constant stress level, as the result of the realignment of crystallographic twins which form during cooling from the austenitic to the martensitic state, in a process known as self-accommodation.

When an article thus deformed is warmed to the temperature at which the alloy starts to revert back to austenite, referred to as the austenite start ($A_s$) temperature, the deformed object will begin to return to its original configuration. With continued heating, the object will reach a temperature referred to as the austenite finish ($A_f$) temperature, at which the reversion to the high temperature configuration is complete.

Nitinol, a nickel-titanium alloy, is one such SMA that has been formed into memory element strips and deployed in the distal ends of catheters. Heating the nitinol memory element strips to a given temperature using an electric current provided by a power supply causes the memory elements to deform to assume a predetermined shape, thereby deflecting the distal end of the catheter. See, for example, U.S. Pat. Nos. 4,543,090; 4,601,705; and 4,758,222 for descriptions of known memory element systems for steering and aiming catheters, cannulae, and the like.

The shape that is recovered by heating is first imparted into the device at high temperature during the manufacturing process. When the device is cooled below its martensite start temperature, it can be distorted into another arbitrary shape. When, however, the device is heated above its austenite start temperature, the imparted shape is partly recovered and, when it is further heated to its austenite finish temperature, the shape is fully recovered. Devices having a distal tip made from SMA utilize these shape memory characteristics to change the shape of the distal tip. Specifically, the SMA guide element is in the martensitic phase during insertion into the body lumen. Application of heat to the guide element causes a phase transformation from the martensitic to the austenitic phase, resulting in the shape of the distal tip being recovered. This change in shape can be used to redirect the device. Shape memory nitinol has previously been used in "strip" or "rod" form in the construction of steerable and aimable devices. Such nitinol strips and rods are solid core guide elements having a circular, rectangular, or other similar cross-sectional shape. In use, these solid core guide elements are placed on opposing sides of a central lumen formed in the device. Selective activation of these guide elements by conversion from martensite to austenite results in articulation of the device. See, for example U.S. Pat. No. 4,601,705 for a disclosure of a four-memory element strip steering and aiming system and U.S. Pat. No. 4,758,222 for a disclosure of a steering and aiming system using a spring and one temperature activated memory element strip.

Devices are also known in which a variable shape guide is constructed from a tube of SMA. One example of such a device is disclosed in U.S. Pat. No. 5,334,168, which describes heating of the SMA tube to cause a phase transformation from the martensitic to the austenitic phase, resulting in shape recovery. The recovered shape allows the device to be redirected through body lumens. However, the preferred embodiments of this patent emphasize that the change in shape of the guide element is effected by the transition of the guide element from the martensitic phase to the austenitic phase.

In the above-mentioned steerable SMA systems the steering means is achieved by heating the SMA while it is in its martensitic form and recovering a different shape as it transforms into its austenitic form. The difficulty with utilizing the transformation from martensite to austenite, or visa versa, to effect shape change and thereby allow for steering is two-fold: firstly the device in its martensitic state is not as springy as in its austenitic state, which makes it more difficult for the operator to manipulate the device from outside the body; secondly, it is difficult to partly transform the SMA to allow for a partial change in shape of the steerable portion of the device. The second shortcoming is due to the fact that shape recovery occurs over the relatively shall temperature range from the austenitic start temperature ($A_s$) to the austenitic finish temperature ($A_f$). Above-mentioned U.S. Pat. No. 5,334,168 also discloses a preferred embodiment in which the tubular guide element comprises superlastic nitinol, which is in the austenitic phase during insertion into the body lumen. The use of superlastic nitinol as the guide element is desirable since such a guidewire has significant axial push and flexibility along its length (bending) while exhibiting excellent torque transmission from the proximal end to the distal end.

However, it is expressly stated in U.S. Pat. No. 5,334,168 at column 4, lines 57 to 64, that heating of the superlastic tubular guide element is not required since superlastic nitinol is already in an activated (austenitic) state.

Accordingly, a guide apparatus as contemplated by this patent having a superlastic nitinol guide element would not take advantage of the shape change which occurs during the heat-induced transformation from martensite to austenite.

What is needed is a system that allows for steering but at the same time maintains the springy qualities of SMA in its austenitic phase. What is also needed is a system that allows for partial changes in the shape of the steerable portion of the device to permit a greater range of steerability.

SUMMARY OF THE INVENTION

The invention herein disclosed is a steerable device that effects shape change entirely while above the austenitic finish temperature and does not rely on recovering the imparted shape at the transition between austenite and martensite. This invention herein disclosed relies on the fact that a tube of SMA in its austenitic form becomes stiffer as the temperature of the material is increased. This increase in stiffness or modulus is approximately linear as a function of increased temperature and therefore allows for a gradual increase in stiffness in response to increases in heat energy applied to the device. For example, if an appropriate force is applied normal to the longitudinal axis of a tube (a bending force) and the tube is made of SMA material that remains in the austenitic phase, when the tube is heated, the tube will become stiffer, partly overcoming the bending force and thereby changing its shape or radius of curvature. This shape change can be used to steer the device. Depending upon the shape of the tube along its longitudinal axis in its unloaded mode and the nature of the impending biasing forces, the tube can be designed to assume many different shapes as it is heated and cooled. The unloaded shape of the SMA tube and the shape of the biasing element can be simple or complex. For example they unloaded SMA tube could be helical, and the biasing element could be contoured to exert the appropriate forces to hold the unit in a straight configuration; upon heating the unloaded helical shape of the SMA tube could come to dominate the shape of the unit.

In summary, the shape change is not due to recovering a shape by heating the SMA between the $A_s$ and the $A_f$ temperature; it is instead a result of the stiffening of the SMA that occurs solely above the $A_f$ while it is in the austenitic phase. It should be noted that this shape change is dependent upon first, a biasing force distorting the SMA device from its unloaded shape (that being the shape it would have at or above the $A_f$ temperature if no biasing force was applied), and second the application of heat to the device causing it to overcome the biasing force somewhat; and moving the device from its distorted shape closer to its unloaded shape.

When such a device is introduced into the bloodstream, the heat applied to the tube would for example be above the temperature of the blood and as more heat is applied to the tube it would become stiffer and with the said appropriate biasing force, the tube would change its shape; but when the heat is removed or reduced, the blood would cool the tube and the tube would become less rigid and more subject to the appropriate biasing force which would tend to return the tube to the same shape it assumed prior to the heat being applied. It can be appreciated that this change of shape can be used for the purpose of steering the distal end of the device; but also this change of shape could occur in a repetitive fashion which would cause the tube to pulse or wriggle. Both of these effects can be utilized to assist in advancing the device along the lumen of the body into which it is introduced. This pulsing or wriggling would reduce the static and dynamic friction at the interface between the device an the wall of the lumen as it is being advanced into the lumen of the vessel.

The use of electricity to heat the said tube has been suggested in a number of patents, including U.S. Pat. No. 5,334,168 referred to above. While one of the preferred embodiments of the invention includes such a heating means, another convenient heating means is described in U.S. Pat. No. 5,846,247 by Unsworth and Waram, incorporated herein by reference. That patent describes how photo-thermal heat produced by a laser is introduced into the lumen of the tube by means of an optical fiber. The said optical fiber directing the photo-thermal energy onto the inside walls of the lumen of the tube by means well known to the art. The heating of the tube can then be controlled in exquisite precision by varying the output of the laser and also perhaps by moving the optical fiber back and forth inside the tube to change the location where the photo-thermal energy is delivered to the said tube. By appropriately changing the part of the tube that is heated, the austenitic tube with appropriate biasing, as described above, could be caused to pulsate or wriggle in addition to pointing in another direction. While reference is made to the methods described in said Unsworth and Waram U.S. Pat. No. 5,846,247, it is to be understood that the preferred embodiments of the invention include any means of heating the tube to cause it to change shape with the appropriate biasing force.

A preferred embodiment of the invention includes a biasing tube, coil or other element that partly or completely surrounds a superlastic SMA tube which becomes stiffer with the application of heat. This biasing tube or element would typically be made of stainless steel, but could be made of plastic or other suitable materials. This tube or element would be typically bent by the surgeon into a curved shape that he might think appropriate to initiate turns for advancing the guide into the lumen of a body vessel.

This bending of the distal end of the guide by the surgeon provides the biasing force that distorts the unloaded shape of the SMA tube. The stainless steel tube or coil although somewhat springy, is bent beyond its yield strength by the surgeon to impart the appropriate curve. However, the superlastic SMA tube being very flexible does not suffer the same plastic deformation due to the said bending. The superlastic tube bends either by elastic deformation of austenite or by the formation of stress-induced martensite from the austenite, in response to the force of the new shape that has been imparted on the biasing element. It is this biasing force that the heating of the SMA tube overcomes to change the shape from the curved shape to a straighter shape in the example above, where the SMA tube was straight in its unloaded shape.

One preferred embodiment of this invention includes an optical fiber that projects photo-thermal energy onto the inside walls of the SMA tube thereby heating the said tube. The projection means are well known to the art and includes the simple projection from the end of the optical fiber, with attendant beam divergence, to side firing means that includes what is referred to in the art as leaky fibers. Leaky fibers being optical fibers that permit the photo-thermal energy to project out the side of the fiber over a determined length.

As described in U.S. Pat. No. 5,846,247 by Unsworth and Waram, the projection of the photo-thermal energy can be modulated while being directed at specific points or along defined tracks as the optical fiber is moved along the inside of the SMA tube being heated. It can be readily seen that a preferred embodiment of this invention might include an optical fiber that moves back in forth inside the SMA tube heating and thereby stiffening only parts of the SMA tube. This selected heating and stiffening would when combined with the forces imparted by the biasing element could result in many desired shapes. The movement of the fiber could be computer controlled and motor driven by means well known to the art. A simpler preferred embodiment of the invention would be comprised of a stationary optical fiber.

Additional features and advantages of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF PREFERRED EMBODIMENTS

Figure 1:
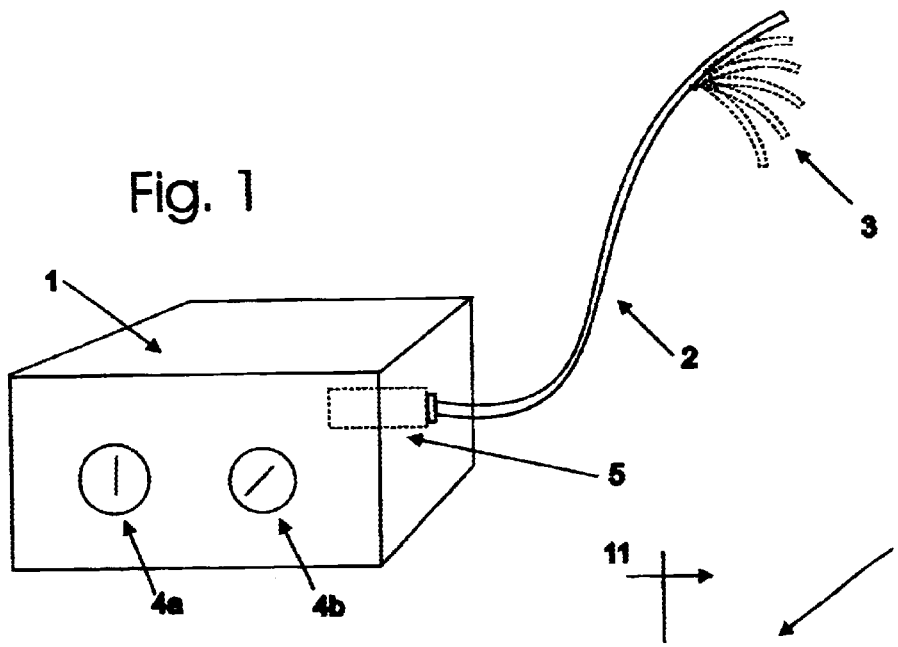
FIG. 1 is a perspective view of a steerable and aimable apparatus according to a first preferred embodiment of the present invention showing the control box 1 that contains a laser 5 and thermal control 4a and pulsing control 4b as well as the guide 2 changing shape at the distal end 3.

An apparatus embodying a first preferred embodiment of the present invention is shown generally in FIG. 1 as being comprised of a control box 1 with a detachably attached tube 2, the distal end of which can articulate at 3. The control box contains a laser 5 that delivers photo-thermal energy to an optical fiber 6 which in turn delivers it to the distal end of the tube 2. The control box 1 also contains means of controlling the amount of photo-thermal energy 4a delivered by the laser to the optical fiber and the pulsing 4b, if any, of the photo-thermal energy delivered to the said optical fiber. Other controls could be included such as a foot-switch or means of controlling various aspects of the photo-thermal energy such as its frequency.

Figure 2:
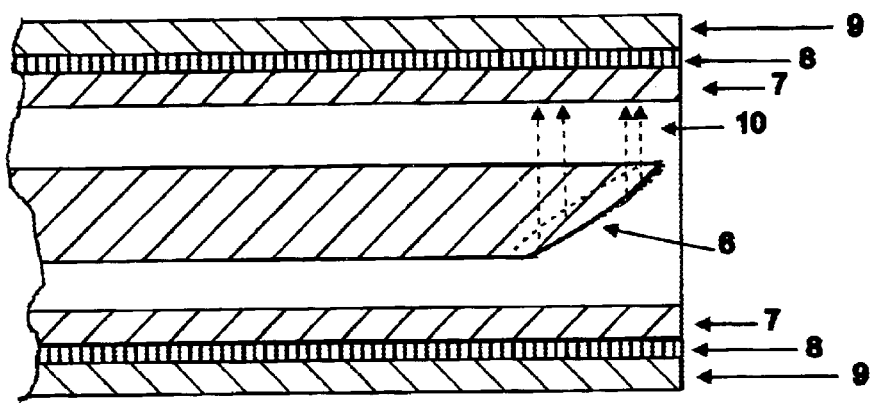
FIG. 2 is an enlarged view of one portion of the distal end of one embodiment of the apparatus in FIG. 1 showing a single SMA tube 7 encased in an thermal insulating barrier 8 both of which are encased in a biasing tube 9. An optical fiber 6 is shown delivering photo-thermal energy 10 to the inside wall of the lumen of the SMA tubing 7.
Figure 3:
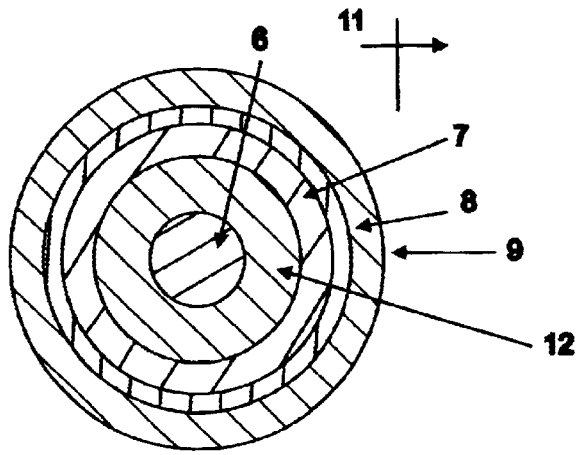
FIG. 3 is a transverse sectional view taken along line 11—11 of FIG. 2 showing the guide 2 with details as noted in FIG. 2.
Figure 4:
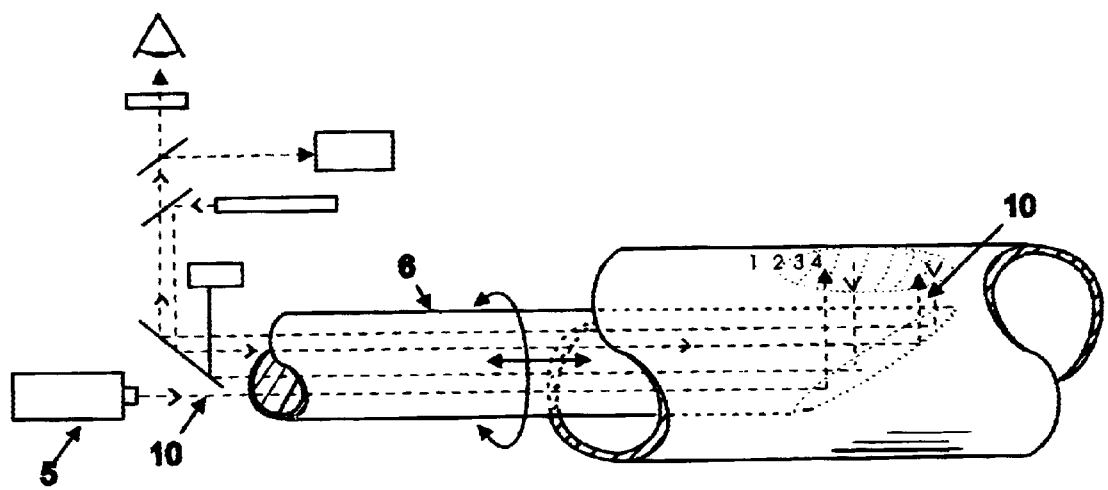
FIG. 4 is a perspective view of a device used in combination with a method taught by Unsworth and Waram in U.S. Pat. No. 5,846,247 for applying thermal energy to the inside of SMA tubes and for heating specific parts of the tubes.

Illustratively, tubular member 2 is formed as shown in FIGS. 2 and 3 to include an optical fiber 6 which can be stationary as shown in FIG. 1, 2, and 3 or can slide back and forth along the longitudinal axis of the tubular member 2 to deliver photo-thermal energy 10 to different parts of the inside wall of the SMA tube 7 as more particularly described in U.S. Pat. No. 5,846,247 and illustrated in FIG. 4. While FIG. 2 shows the photo-thermal energy 10 being directed to only the upper portion of the tube, the distal end of optical fiber 6 could also project the photo-thermal energy to all sides of the inside of the tube using a leaky fiber tip, well known to the art, or by simply allowing the photo-thermal energy to project out a cut end of the distal tip of the optical fiber 6 and relying on the divergence of the beam to project the photo-thermal energy onto the inside walls of the lumen of the SMA tube 7. As referred to above, the heating of the SMA tube 7 by the photo-thermal energy causes the tube which is in its austenitic phase to stiffen and act against the biasing force that has been imparted to the biasing tube 9. The SMA tube 7 could be separated from the biasing tube 9 by an insulating material 8. This insulating material 8 would prevent excess heat from being transferred to the body into which the tubular member 2 in inserted. The insulating material could also be added to outside layer of the tubular member 2 if required with the inner layer of insulating material either present or absent. The biasing tube 9 could be a tube as shown in FIG. 2 and 3 or could be a coil, mesh, tape or strip or other suitable biasing element. The biasing tube as noted above must impose a bending moment on the SMA tube 7 so that the SMA tube 7 when heated can stiffen and partly overcome or work against the said bending moment and thereby change the shape of the distal end of the tube 2 and permit the steering or aiming of the distal end of tube 2. The biasing tube 9 will thus principally impose a shape of the distal end of tube 2 when the SMA tube is not being actively heated by the application of photo-thermal energy 10. This will cause the springy and relatively flexible SMA tube 7 to bend from its unloaded austenitic state. As photothermal energy is applied to the inside of the SMA tube 7 it will stiffen and overcome the force applied by the biasing tube, changing the shape closer to that of the SMA tube 7 when in its unloaded austenitic shape. Naturally the biasing tube 9 must exert just the right range of forces to allow the SMA tube 7 to move the biasing tube when heated, but to be overcome by the biasing element when cooled. As the SMA tube 7 gets stiffer as a function of the amount of heating, the distal tip of tube 2 can take a range of shapes. Conversely when the photo-thermal heating is reduced or turned off, approximately the reverse sequence of shapes are produced.

As noted above the heating can also be pulsed and moved to create a vibrating or wriggling distal tip which may be of use for certain purposes. The biasing tube can have a preset shape or can be shaped by the surgeon to a shape that best suits his purpose.

While the preferred embodiment includes the use of nickel-titanium in the tube 7 other materials that exhibit changes in modulus in response to change in temperatures, such as shape memory plastics, could also be used without departing from the scope of the invention.

While the preferred embodiment indicates tubes in a particular order it should be noted that the tubes can be in any order that is convenient for the particular use to which the device is employed. It should also be noted that preferred embodiments of the invention may contain elements that are not tubes, for example the biasing element or the insulating layers may be tapes, meshes, strips or other elements that are not formed into a tubes but serve the same or similar purposes.

While the first preferred embodiment discussed above utilizes photo-thermal heating, other means of heating the SMA tube could also be used including electricity and chemical reactions. Illustrated in FIGS. 5 and 6 is a second preferred embodiment of the invention in which a the distal end of a guidewire is heated electrically by stationary heating means.

Figure 5:
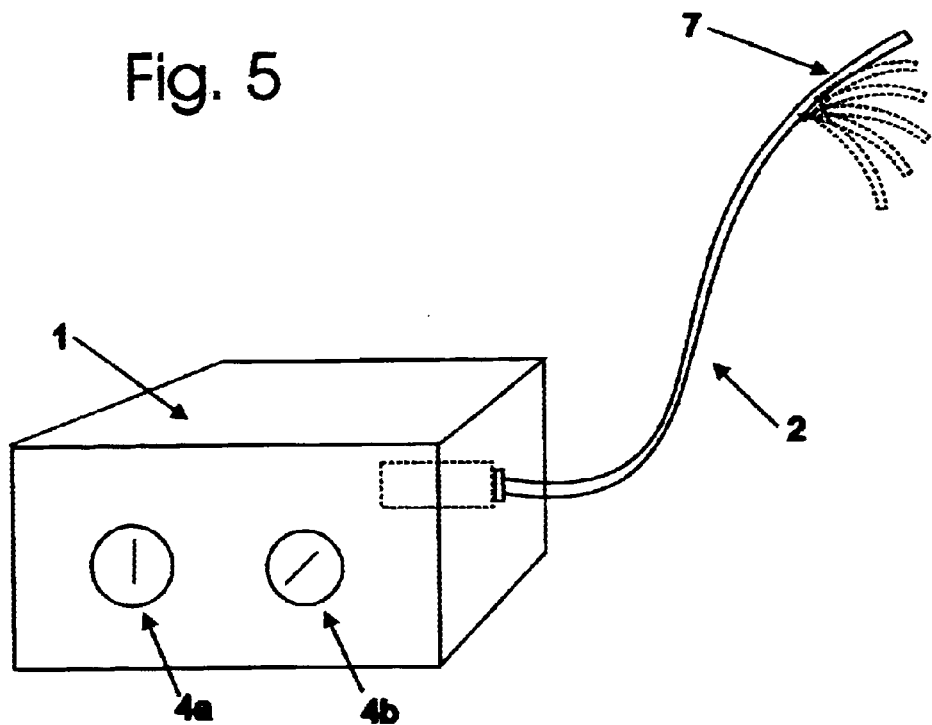
FIG. 5 is a perspective view of a steerable and aimable apparatus according to a second preferred embodiment of the present invention.

An apparatus embodying the second preferred embodiment is shown generally in FIG. 5 as comprising a control box 1 with a detachably attached guidewire 2 in the form of a tube, at least the distal end of which is comprised of a superlastic shape memory alloy tube 7. The control box 1 delivers electrical energy to heat the SMA tube 7. As in the first preferred embodiment, control box 1 also comprises means 4a for controlling the amount of electrical energy delivered to the SMA tube 7, and means 4b for pulsing the electrical energy delivered to the SMA tube 7. Other controls could also be included, such as a foot switch or other means of controlling various other parameters of the electrical energy delivered to the SMA tube 7.

Figure 6:
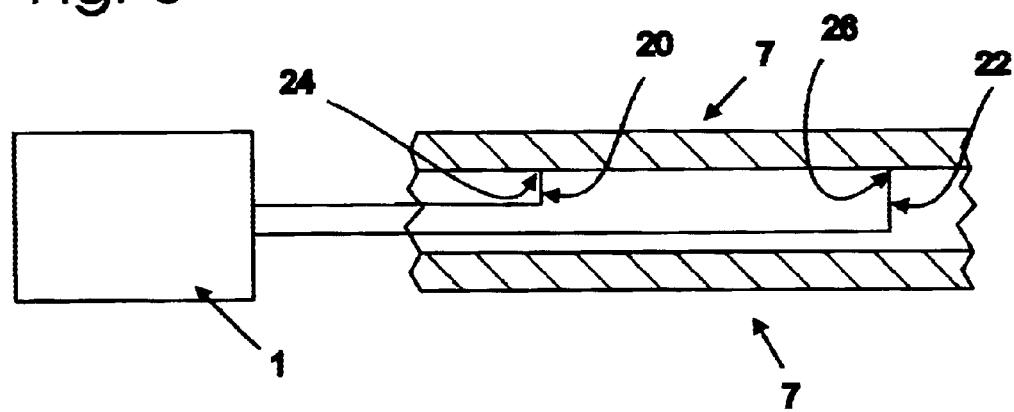
FIG. 6 is an enlarged side sectional view of a distal end of the apparatus shown in FIG. 5.

As illustrated in FIG. 6, a pair of conductors 20 and 22 extend from the control box, through the lumen of the guidewire 2 to the SMA tube 7 located at the distal end thereof. The distal ends of the conductors are in electrical contact with the inner surface of the SMA tube 7, and may be attached thereto by any suitable means, such as welding, thereby forming an electrical circuit which includes at least a portion of the SMA tube 7.

The points 24 and 26 on the inner surface of SMA tube 7 at which conductors 20 and 22 are attached are spaced from one another such that electrical energy flowing between points 24 and 26 causes resistive heating of the SMA tube 7 between points 24 and 26, thereby resulting in stiffening of the SMA tube 7 as described above in the first preferred embodiment. Preferably, as shown, point 26 at which conductor 22 is attached to the SMA tube 7 is at or proximate the distal tip of the guidewire 2, and the point 24 at which conductor 20 is attached is spaced from point 26 toward the proximal end of guidewire 2.

In the second preferred embodiment, the guidewire 2 is not provided with an outer biasing tube 9 to cause deformation of the SMA tube 7. It will be appreciated that deformation of the guidewire 2, and the SMA tube 7 at the distal end thereof, will occur during insertion of the guidewire 2 into a body lumen such as a blood vessel. Activating the electrical heating means to heat the SMA tube above the temperature of the blood in the blood vessel causes stiffening and straightening of the SMA tube, while deactivating the heating means results in cooling of the SMA tube, again making it subject to deformation. The heating and cooling and resulting straightening and deformation of the SMA tube 7 results in movement of the SMA tube 7 as discussed above with reference to the first preferred embodiment.

Although the second preferred embodiment as described above does not include a biasing tube, it will be appreciated that the guidewire according to the second preferred embodiment may also be provided with a biasing tube as described in the first preferred embodiment.

Furthermore, it will be appreciated that the guidewire 2 according to the second preferred embodiment, including the steerable SMA tube 7, is not necessarily tubular and could alternatively be in strip or rod form, as described above. In such an embodiment, the electrical energy could be delivered through conductors extending along the outside or through the guidewire to the distal tip thereof, and the guidewire and conductors could optionally be encased inside a biasing tube along at least a portion of its length.

While the preferred embodiments of the invention relate to an apparatus with a steerable or aimable tip comprised of a SMA tube 7 with or without a biasing tube 9 and insulating tube or layer 8, it should be noted that other preferred embodiments include these elements only in the part of the tubular guidewire 2 that is steerable or aimable, that is in the distal end of the said tubular member. The part of the tubular member proximal to the part that is steerable or aimable need not be composed of these elements and may be comprised of plastic tube or metal tubes, these tubes being connected by the usual means to the said elements that make up the steerable or aimable distal portion.

It should also be noted that preferred embodiments of the present invention may include coatings to increase the lubricity or bio-compatibility of the apparatus. While the preferred embodiments describes systems having one heating means and one lumen, the system could have one or more heating means and one or more lumens so that movement in various directions could be achieved. While the preferred embodiment describes a guide, it is to be understood that the apparatus could be used as a catheter to deliver drugs or other devices to body lumens or for any other purpose where a steerable or aimable device is useful.

While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. An apparatus for insertion in a body lumen, the apparatus having a steerable distal end portion comprising:
    an elongate shape memory member having a proximal end and a distal end, the elongate shape memory member being comprised of a shape memory alloy which adopts a memorized shape in an unloaded austenitic state, the shape memory alloy having an austenite finish temperature less than a temperature inside the body lumen; and
    stationary heating means for heating at least a portion of the elongate shape memory member to a temperature above the temperature inside the body lumen;
    wherein heating the elongate shape memory member inside the body lumen causes it to increase in stiffness and tend toward the memorized shape, and subsequent discontinuation of heating causes the elongate shape memory member to decrease in stiffness, allowing the distal end portion to be deformed from the memorized shape.

2. The apparatus of claim 1, wherein the elongate shape memory member is tubular, having a lumen extending therethrough.

3. The apparatus of claim 1, wherein the heating means comprises electrical heating means.

4. The apparatus of claim 3, further comprising:
    electrical supply means to provide electrical energy for heating the elongate shape memory member; and
    electrical conductor means for transferring the electrical energy from the supply means to the elongate shape memory member.

5. The apparatus of claim 4, wherein the electrical conductor means comprises a first electrical conductor and a second electrical conductor, each of the electrical conductors being in electrical contact with the elongate shape memory member.

6. The apparatus of claim 5, wherein the first electrical conductor is in electrical contact with a first point on the elongate shape memory member proximate the distal end thereof, and the second electrical conductor is in electrical contact with a second point on the elongate shape memory member, the second point being spaced from the first point toward the proximal end of the elongate shape memory member.

7. The apparatus of claim 5, wherein the elongate shape memory member is tubular, having a lumen extending therethrough, and wherein the first electrical conductor and the second electrical conductor extend through the lumen of the elongate shape memory member.

8. The apparatus of claim 6, wherein the elongate shape memory member is tubular, having a lumen extending therethrough and a cylindrical inner wall, and wherein the first electrical conductor and the second electrical conductor extend through the lumen of the elongate shape memory member and the first and second points are located on the cylindrical inner wall of the elongate shape memory member.

9. The apparatus of claim 1, further comprising heating control means to control the intensity and duration of heat applied to the elongate shape memory member by the heating means.

10. The apparatus of claim 9, where in the heating control means causes intermittent operation of the heating means such that heat is applied to the elongate shape memory member in short pulses separated by periods in which the elongate shape memory member is allowed to cool, resulting in continuous, repetitive movement in the distal end portion.

11. The apparatus of claim 10, wherein the heating control means simultaneously varies one or more of the intensity and duration of the heat applied to the elongate shape memory member by the heating means.

12. The apparatus of claim 1, wherein the shape memory alloy comprising the elongate shape memory member has an austenite finish temperature less than human body temperature, and wherein the steerable distal end portion of the apparatus has a diameter which allows it to be guided through blood vessels of a human patient.

13. The apparatus of claim 1, wherein the shape memory alloy comprising the elongate shape memory member is a nickel-titanium alloy.

14. The apparatus of claim 1, wherein the memorized shape is substantially straight.

15. A system for guiding devices or materials into a body lumen, comprising:
   a guidewire having a proximal end, a distal end spaced from the proximal end, and one or more lumens extending through the guidewire from the proximal end to approximately the distal end, wherein the guidewire is comprised of a shape memory alloy (SMA) or other shape memory material, the guidewire having a memorized shape and being deformable from the memorized shape as it follows curves in the body lumen the deformation tending toward stress-induced martensite, and the memorized shape being at least partly recoverable by the application of thermal energy to the guidewire in its deformed state;
   characterized in that:
   the system further comprises electrical heating means adapted for localized heating of the guidewire to overcome stress caused by deformation of the guidewire and return all or part of the guidewire to its memorized shape; and
   a temperature of the body lumen is greater than an austenite finish temperature of the shape memory alloy or other shape memory material.

16. The system of claim 15, wherein the memorized shape is substantially straight.

17. The system of claim 15, wherein the heating means comprises stationary electrical heating means.

18. The system of claim 17, further comprising:
   electrical supply means connected to the proximal end of the guidewire to provide electrical energy for heating the guidewire; and
   electrical conductor means for transferring the electrical energy from the supply means to the distal end of the guidewire.

19. The system of claim 18, wherein the electrical conductor means comprises a first electrical conductor and a second electrical conductor, each of the electrical conductors being in electrical contact with the distal end of the guidewire.

20. The system of claim 19, wherein the first electrical conductor is in electrical contact with a first point on the distal end of the guidewire, and the second electrical conductor is in electrical contact with a second point on the distal end of the guidewire, the second point being spaced from the first point toward the proximal end of the guidewire.

21. The system of claim 20, wherein the first electrical conductor and the second electrical conductor extend through the lumen of the guidewire.

22. The system of claim 21, wherein the first and second points are located on a cylindrical inner wall of the guidewire.

23. The system of claim 15, further comprising heating control means to control the intensity and duration of heat applied to the distal end of the guidewire by the heating means.

24. The system of claim 23, wherein the heating control means causes intermittent operation of the heating means such that heat is applied to the distal end of the guidewire in short pulses separated by periods in which the distal end of the guidewire is allowed to cool, resulting in continuous, repetitive movement in the distal end of the guidewire.

25. The system of claim 24, wherein the heating control means simultaneously varies one or more of the intensity and duration of the heat applied to the distal end of the guidewire by the heating means.

26. The system of claim 15, wherein the shape memory alloy comprising the guidewire has an austenite finish temperature less than human body temperature, and wherein the distal end of the guidewire has a diameter which allows it to be guided through blood vessels of a human patient.

27. The system of claim 1, wherein the shape memory alloy comprising the guidewire is a nickel-titanium alloy.

* * * * *